US012765880B2

(12) United States Patent
Tepic et al.

(10) Patent No.: US 12,765,880 B2
(45) Date of Patent: Oct. 20, 2026

(54) SAW BLADE FOR TIBIAL PLATEAU LEVELING OSTEOTOMY

(71) Applicant: KYON AG, Zürich (CH)

(72) Inventors: Slobodan Tepic, Zürich (CH); Stephen Bresina, Davos (CH)

(73) Assignee: KYON AG, Zürich (CH)

( * ) Notice: Subject to any disclaimer, the term of this patent is extended or adjusted under 35 U.S.C. 154(b) by 451 days.

(21) Appl. No.: 18/006,016

(22) PCT Filed: Jul. 28, 2021

(86) PCT No.: PCT/EP2021/071164

§ 371 (c)(1),
(2) Date: Jan. 19, 2023

(87) PCT Pub. No.: WO2022/023421

PCT Pub. Date: Feb. 3, 2022

(65) Prior Publication Data

US 2023/0346390 A1 Nov. 2, 2023

(30) Foreign Application Priority Data

Jul. 29, 2020 (EP) ..................................... 20188448

(51) Int. Cl.
*A61B 17/14* (2006.01)
*A61B 17/15* (2006.01)
(Continued)

(52) U.S. Cl.
CPC .......... *A61B 17/142* (2016.11); *A61B 17/152* (2013.01); *A61B 17/157* (2013.01);
(Continued)

(58) Field of Classification Search
CPC ...... B23D 51/10; B23D 51/01; B23D 61/123; B23D 61/006; B23D 61/025; B23D 49/10; B23D 49/11; B23D 49/56; B23D 57/00; B23D 67/04; B23D 45/044; B23D 45/048; B26D 7/086; B26D 2001/006; B26B 9/00; B26B 9/02; B26B 5/00; B26B 25/002; B26B 21/56; B26B 21/225; B26B 21/521;
(Continued)

(56) References Cited

U.S. PATENT DOCUMENTS 3,758,222 A * 9/1973 Oakes .................. B23B 51/009 408/224
4,409,973 A 10/1983 Neufeld
(Continued)

FOREIGN PATENT DOCUMENTS

CN 205626016 U 10/2016
CN 110313972 A2 10/2019
(Continued)

OTHER PUBLICATIONS

Extended European Search Report issued in EP20188448.3 dated Feb. 2, 2021, 9 pages.
(Continued)

*Primary Examiner* — Marcela I. Shirsat
(74) *Attorney, Agent, or Firm* — Klarquist Sparkman, LLP

(57) ABSTRACT

The present invention provides a surgical instrument for performing closing wedge osteotomies by a single step procedure.

18 Claims, 8 Drawing Sheets

(51) Int. Cl.

| | |
|---|---|
| ***A61B 17/16*** | (2006.01) |
| ***A61B 17/32*** | (2006.01) |
| ***A61B 17/56*** | (2006.01) |
| ***B23D 61/00*** | (2006.01) |
| ***B23D 61/02*** | (2006.01) |
| ***B23D 61/12*** | (2006.01) |
| ***B23D 67/04*** | (2006.01) |
| ***B26B 21/56*** | (2006.01) |
| ***B26D 1/00*** | (2006.01) |

(52) U.S. Cl.

CPC .......... *A61B 17/1637* (2013.01); *A61B 17/14* (2013.01); *A61B 17/147* (2016.11); *A61B 17/154* (2013.01); *A61B 17/155* (2013.01); *A61B 17/1657* (2013.01); *A61B 17/1659* (2013.01); *A61B 17/1662* (2013.01); *A61B 17/32* (2013.01); *A61B 17/32002* (2013.01); *A61B 2017/320028* (2013.01); *A61B 2017/564* (2013.01); *B23D 61/006* (2013.01); *B23D 61/025* (2013.01); *B23D 61/123* (2013.01); *B23D 67/04* (2013.01); *B26B 21/56* (2013.01); *B26D 2001/006* (2013.01); *Y10T 83/4749* (2015.04); *Y10T 83/6985* (2015.04); *Y10T 83/7045* (2015.04); *Y10T 83/8798* (2015.04); *Y10T 83/9481* (2015.04)

(58) Field of Classification Search

CPC ....... B25G 3/00; A61B 17/3213; A61B 17/14; A61B 17/142; A61B 17/147; A61B 17/152; A61B 17/157; A61B 17/154; A61B 17/155; A61B 17/1637; A61B 17/1657; A61B 17/1662; A61B 17/1659; A61B 17/32; A61B 17/32002; A61B 2017/320028; A61B 2017/00477; A61B 2017/564; Y10T 83/4749; Y10T 83/6985; Y10T 83/7045; Y10T 83/7788; Y10T 83/7793; Y10T 83/8798; Y10T 83/9481

See application file for complete search history.

(56) References Cited

U.S. PATENT DOCUMENTS

| | | | | |
|---|---|---|---|---|
| 4,677,973 | A | 7/1987 | Slocum | |
| 4,955,888 | A | 9/1990 | Slocum | |
| 6,379,371 | B1 | 4/2002 | Novak et al. | |
| 8,939,981 | B1 * | 1/2015 | Anderson .............. | A61B 17/14 606/82 |
| 10,702,283 | B2 | 7/2020 | Sidebotham et al. | |
| 2002/0133186 | A1 | 9/2002 | Kullmer | |
| 2009/0044679 | A1 * | 2/2009 | Souza .................. | B23D 61/123 83/661 |
| 2016/0128745 | A1 | 5/2016 | Sidebotham et al. | |
| 2018/0125503 | A1 * | 5/2018 | Sidebotham ......... | A61B 17/147 |
| 2021/0000486 | A1 * | 1/2021 | Cundiff ................ | A61B 17/142 |
| 2021/0030435 | A1 | 2/2021 | Cao et al. | |

FOREIGN PATENT DOCUMENTS

| | | | |
|---|---|---|---|
| DE | 202007010079 | U1 | 11/2007 |
| EP | 2854677 | B1 | 4/2016 |
| JP | 2013-537091 | A | 9/2013 |
| JP | 6 431 641 | B1 | 11/2018 |

OTHER PUBLICATIONS

International Search Report issued in PCT/EP2021/071164 dated Oct. 18, 2021, 16 pages.

Slocum et al. "Tibial Plateau Leveling Osteotomy for Repair of Cranial Cruciate Ligament Rupture in the Canine", Vet. Clin. North Am., vol. 23, No. 4, 1993, pp. 777-795.

Slocum et al. "Cranial Tibial Wedge Osteotomy: A Technique for Eliminating Cranial Tibial Thrust in Cranial Cruciate Ligament Repair", J. Am. Vet. Med. Assoc., vol. 184, No. 5, 1984, pp. 564-569.

Tepic et al., "Biomechanics of the Stifle Joint", 1st World Orthopaedic Veterinary Congress, Munich, Germany, 2002, pp. 189-190.

Randy J. Boudrieau "Tibial Plateau Leveling Osteotomy or Tibial Tuberosity", Veterinary Surgurgey, 38, 2009, pp. 1-22.

* cited by examiner (a)

(b)

SAW BLADE FOR TIBIAL PLATEAU LEVELING OSTEOTOMY

This application is a 35 U.S.C. 371 National Phase Entry Application from PCT/EP2021/071164 filed Jul. 28, 2021, which claims priority to and the benefit of European Patent Application No. 20188448.3, filed on Jul. 29, 2020, the disclosures of which are incorporated herein by reference in their entirety.

FIELD OF THE INVENTION

The present invention relates to a surgical saw blade useful in treating disorders of the knee, termed the stifle in dogs, which facilitates performing Tibial Plateau Leveling Osteotomy (TPLO) with a preset closing wedge angle to compensate for the TPLO induced valgus that results from use of conventional saw blades.

BACKGROUND OF THE INVENTION

The anterior cruciate ligament (ACL) in the human knee joint, commonly called the cranial cruciate ligament (CrCL) in the canine stifle, is frequently torn in trauma. It also frequently fails, particularly in dogs, after a degenerative process of still unknown etiology.

In human orthopedics, standard procedures replace the failed ACL with an ACL allograft or an autograft made from a part of the patient's own patellar tendon or a part of the fascia and tendon removed from the hamstring muscles. The procedure results in a stable knee, but the long-term performance of the knee is often unsatisfactory. Roughly, 75-90% of cases result in degenerative arthritis of the joint within 15 years of the procedure.

In dogs, the standard procedure involves either placement of an extra-capsular suture or performance of one of several geometry-modifying surgical techniques. In the extra-capsular procedure, a suture is placed outside of the joint, usually on the lateral side, to approximate the function of the CrCL. The intention of the suture application is to provide stability of the joint for several weeks while waiting for fibrosis to occur around the joint. This fibrosis should then provide for long-term stability. However, the extra-capsular suture technique regularly results in failure. Degenerative arthritis of the joint, after a year or so, is the rule rather than the exception.

Attempts to replace the CrCL in the dog by an anatomically placed, intra-articular artificial ligament have also generally failed in spite of years of research and development of materials, anchor designs, and surgical techniques.

In surgical, geometry-modifying techniques, the tibia is cut and a segment of it is repositioned to change the geometry of the tibia and/or the joint in order to stabilize the stifle. Various techniques have been used, including tibial plateau leveling osteotomy (TPLO; see U.S. Pat. No. 4,677,973 and Slocum and Slocum, *Vet. Clin. North Am.* 23:777-795, 1993), cranial closing wedge osteotomy (CWO; Slocum and Devine, *J. Am. Vet. Med. Assoc.* 184:564-569, 1984), and tibial tuberosity advancement (TTA; Tepic et al., *Biomechanics Of The Stifle Joint*, in Proceedings of the 1st World Orthopaedic Veterinary Congress, Munich, Germany, pp. 189-190. 2002; see EP 2854677 B1, Tepic and Hopmans). Of the surgical approaches used in dogs, TTA seems to be associated with less morbidity and faster recovery, and it also provides immediate and durable stability to the joint (Boudrieau, *Vet Surg.,* 38(1):1-22, 2009). TPLO with more than a decade advantage in terms of clinical acceptance is the most commonly used geometry-modifying procedure.

Nevertheless, surgical complications are not uncommon with all these techniques. The most common is post-surgical damage to the medial meniscus caused by excessive, supra-physiological movement between the femur and the tibia. Failure of the fixation of TPLO by special plates and screws is relatively rare, but when it does occur, it is usually on the proximal segment and is very difficult to treat by revision procedure for lack of good bone purchase proximally to the osteotomy.

SUMMARY OF THE INVENTION

The present invention provides instruments and methods for surgically treating a partial or complete rupture of the cranial cruciate ligament (CrCL) by TPLO by correcting the valgus deformity at the stifle, which is an unintended consequence of performing TPLO using a conventional saw blade. The mechanical consequence of this valgus deformity is a lateral shift of the joint reaction force, which then causes an even higher tendency towards valgus. The lateral support at the osteotomy is greatly reduced by the TPLO rotation, so much so that the lateral cortices of the proximal and distal tibia segment cross at only two points at the osteotomy. Crushing of the bone at these points leads to even more valgus exposing the fixation by the screws of the TPLO plate to high pullout and bending forces. Even worse, it is mostly the one crossing of the cortices located in the caudal aspect of the saw cut that takes the brunt of the joint load. If a failure does occur, it is typically at the proximal segment of the tibia where the cortical bone is very thin, and the screws engage mostly in weak cancellous bone.

Clear indications of this mode of failure were observed in numerous in vitro experiments we have conducted wherein the hind limbs of dogs were tested to failure comparing intact limbs to those altered by the TPLO procedure. Typically, the TPLO constructs failed at about 50% of contralateral, intact limbs. This is in stark contrast to TTA constructs the strength of which were about 100% of intact. The reason for this major difference is that TTA does not disrupt the congruency of the joint and there is no deviation in position of the stifle in the transverse plane, i.e. the leg remains in the natural position within the sagittal plane.

This observation from experimental studies agrees with observations from clinical failures of TPLO. Even if no failure of the fixation develops, careful examination of TPLO cases frequently shows the partial collapse of the lateral support with the cortices cutting into each other and thus leading to furthering valgus deviation at the stifle. Another potential reason for TPLO-induced valgus is the very different shape of the medial and the lateral tibial condyles. Both condyles are convex, but the lateral condyle's convexity is much higher. The rotation at the osteotomy by TPLO procedure changes the position of contacts between the femoral and tibial condyles resulting in the relative lowering of the lateral femoral condyle, which in an intact joint, rides on the high section of the tibial lateral condyle. This can also induce forced internal rotation of the tibia.

While it is possible to perform TPLO with so-called double cuts to correct for major varus or valgus deformities, the correction needed for this problem that seems to be a universal consequence of stifle anatomy and mismatch of cortices on the lateral side after TPLO rotation is small and hence difficult to treat with double osteotomies.

The present invention solves the problem by the design of a TPLO saw blade, which is wedge-shaped and leads to a pre-set correction. At the leading edge, the blade is of uniform thickness, generally 1 mm or less. Further away from the leading edge toward the upper end, the blade thickness increases. In certain embodiments, the blade thickness increases not uniformly over its whole breadth—at the side edges the thickness may be the same as at the leading edge, but in the middle, it gains in thickness. At the average depth of the finished cut, the blade has the same radius of the inner and the outer surface, just as in the original Slocum bi-radial saw blade (U.S. Pat. No. 4,955,888, Biradial saw, D. Barclay Slocum, Sep. 11, 1990). For manufacturing reasons, the inner surface of the saw blade may be cylindrical while the outside surface of the blade is 3D-shaped to result in the desired cut geometry and provided with a multitude of teeth to gradually remove the bone as the blade is advanced from the medial towards the lateral aspect of the proximal tibia. In short, to the surgeons familiar with the subject, the blade of this invention can be described as a TPLO saw blade that changes gradually with distance from the leading edge of a conventional saw blade to the Slocum biradial saw blade at the depth of the average full-thickness cut.

With the shape of the cross-section of the tibia at the level of a TPLO where the cortices on the lateral side cross at only two points, at best, it is of less importance that the saw blade is not of Slocum's biradial type on the lateral side. On the medial side, cortices align over a much longer part of the cut so having better contact resulting from the biradial shape of the saw blade is more consequential.

With the same technical approach to manufacturing, a flat, oscillating saw blade can be made to execute precise planar closing wedge osteotomies. In some cases, involving major deformities, large angles of closing wedge osteotomies are called for and those are best performed by double planar cuts. However, if less than 10 degrees are planned for, making a single cut with a special blade according to the present invention is of real benefit. Such blades can be made with several angles with for example increments of 2 to 3 degrees.

A first aspect of the present invention relates to an oscillating saw blade adapted for use in bone surgery comprising an upper end, a lower end, an outside face, and an inside face, wherein at the lower end a leading edge with cutting teeth is provided. At the upper end, the saw blade may comprise an element, e.g. a roof and a hub for connection to an oscillating saw machine, which may typically comprise a drive unit and a hand grip.

The term "oscillating saw blade" in the context of the present invention refers to a saw blade adapted for an oscillatory movement. The oscillating saw blade is adapted for use in medicine, e.g. in human or veterinary medicine, particularly for use in bone surgery, more particularly for bone surgery in dogs. In certain embodiments, the saw blade is sterilized and optionally packaged.

In particular embodiments, the present invention relates to a saw blade adapted for an oscillatory movement in bone surgery, wherein its thickness increases from the leading edge at its lower end towards its upper end, wherein the blade is of curved shape.

In certain embodiments, the outside face of the saw blade, at least on the portion toward the leading edge is provided with cutting teeth. Further, a plurality of windows may be provided through the full thickness of the blade.

According to the present invention, the thickness of the saw blade, i.e. the distance between the outside face and the inside face increases from the leading edge at its lower end towards the upper end. Thus, in a longitudinal cross-section, the saw blade of the invention has a wedge shape, wherein the narrowest part of the wedge is at the leading edge at its lower end. In certain embodiments, the thickness of the saw blade at the leading edge is about 1 mm or less, preferably about 0.5 to about 0.9 mm and more preferably about 0.7 mm. The angle corresponding to the increase in thickness is in the range of about 2 to about 10 degrees, preferably about 3 to about 8 degrees and more preferably about 5 degrees.

In certain embodiments, the thickness increases in steps, wherein a plurality, e.g. 2 or more, e.g. 5 or more discrete steps are provided on the outside face of the saw blade. At the leading edges of the steps, cutting teeth are provided. The steps may be in the size range of 0.1 to 1.0 mm, preferably in the range of 0.3 to 0.5 mm, most preferably about 0.4 mm.

In certain embodiments, the blade is of curved shape, wherein the outside face is convex and the inside face is concave. The curved shape may be adapted for use in a surgical procedure involving cutting of a bone, e.g. Tibial Plateau Leveling Osteotomy (TPLO) procedure or planar closing wedge osteotomy.

In certain embodiments, the blade thickness at the leading edge is uniform while the blade thickness increases in steps away from the leading edge in its central portion but not along its longitudinal edges, i.e. the edges ranging from the upper end to the lower end of the saw blade. The shape of the cross-section at the trailing end may be of biradial, Slocum type, wherein the radius of curvature of the concave surface is equal to the radius of curvature of the convex surface.

In certain embodiments, the blade is substantially planar or planar.

A further aspect of the invention relates to a Tibial Plateau Leveling Osteotomy (TPLO) procedure, which is performed with an oscillating saw blade as described above.

Still a further aspect of the present invention is a planar closing wedge osteotomy, which is performed with an oscillating blade as described above.

DETAILED DESCRIPTION

This invention is based, at least in part, on in vitro experiments and clinical observations that have helped us identify the fundamental causes of the mechanical failures of the TPLO procedure.

Our experimental work with dog cadavers, with the hind leg loaded in a testing machine in compression between the femoral head and the hock joint, has shown a strong tendency of the TPLO constructs to a valgus drift at the stifle. Intact legs do not show that tendency and on average need twice the load to failure in comparison to TPLO. With the stifle moving into valgus position the load across the stifle joint shifts laterally and hence creates even higher loading of the weakly supported lateral side. The cortices on the lateral side cut into each other. The TPLO plate is fixed on the medial side and the collapsing support on the lateral side places the plate under bending and the screws under bending and pullout forces. The critical fixation is usually proximally with the weaker, cancellous bone for screw anchorage. Proximal screws are also placed at a short distance to each other. This can result in a pullout of the screws or ripping out of a larger piece of bone from the proximal tibia. Another consequence of the lateral collapse is occasionally observed fracture of the fibula, which is of some real clinically negative impact.

A moderate closing wedge of preferably about 5 degrees on the medial side of the cut results in the medial shift of the joint load sparing the lateral cortices overload. As a practical consequence, the proximal screws pullout loading is much reduced, paving the way for using mono-cortical screws in both proximal and distal segments. This can spare the time in surgery but also reduce some risks of drilling for and using bi-cortical screws. The most cranial screw in the proximal segment of TPLO in many cases exits on the lateral side just under the tendon of the long digital extensor. A long screw can cause damage or even rupture of this tendon.

In many instances, the most caudal screw line of insertion is very close to hitting the fibula. In our in vitro experiments, dissections have shown a number of cases where the drill bits have done damage to the fibula due to uncontrolled penetration of the drill bit past the lateral cortex. This was observed with the surgeries performed by very experienced surgeons and different plate designs.

The further benefit of using mono-cortical screws is the reduced cost of implants with a greatly reduced inventory of the screws of different lengths.

Figure 1:
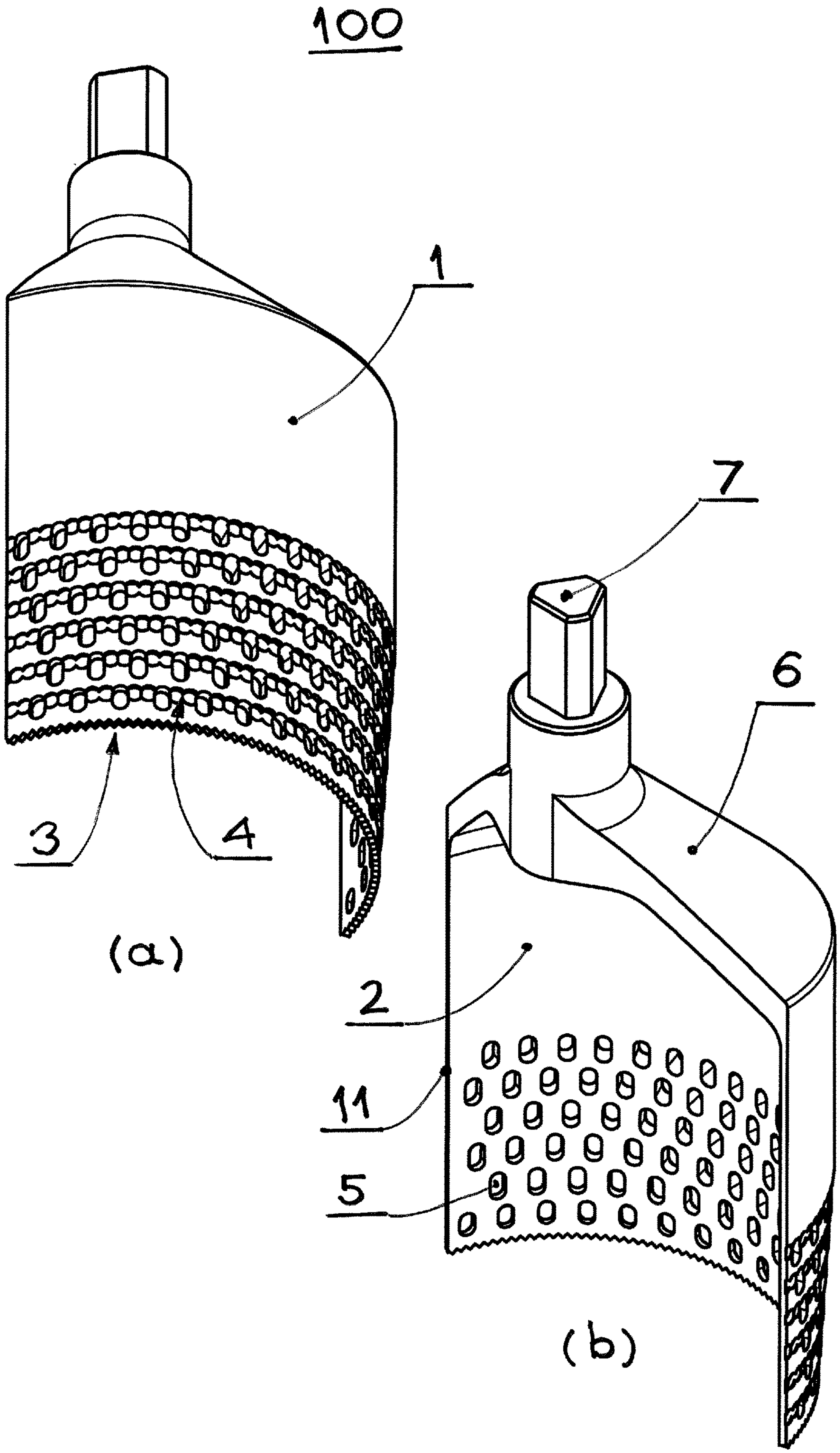
FIG. 1 shows perspective views of a curved TPLO saw blade from outside and inside.

FIG. 1 shows two perspective views of the curved TPLO saw blade 100—the view (a) is from the outside, convex side 1 of the saw blade; the view (b) is from the inside, concave side 2 of the saw blade. The leading edge of the saw blade is provided with fine cutting teeth 3. Up to about a half of the saw blade length, the outside face 1 of the saw blade 100 is provided by stepwise distributed cutting teeth 4 formed by flat ended cylindrical mill cutting the steps of the saw blade down to just below the surface of the step distal to the level of the teeth (see FIG. 5). For easier removal of the bone debris, a number of windows 5 are cut through the full thickness of the saw blade. Thickness of the blade along the longitudinal edges 11 is constant and equal to the thickness at the leading edge.

A conventional dome-shaped roof 6 of the saw blade connects the blade to the hub 7 used to attach the blade to the oscillating saw machine.

Figure 2:
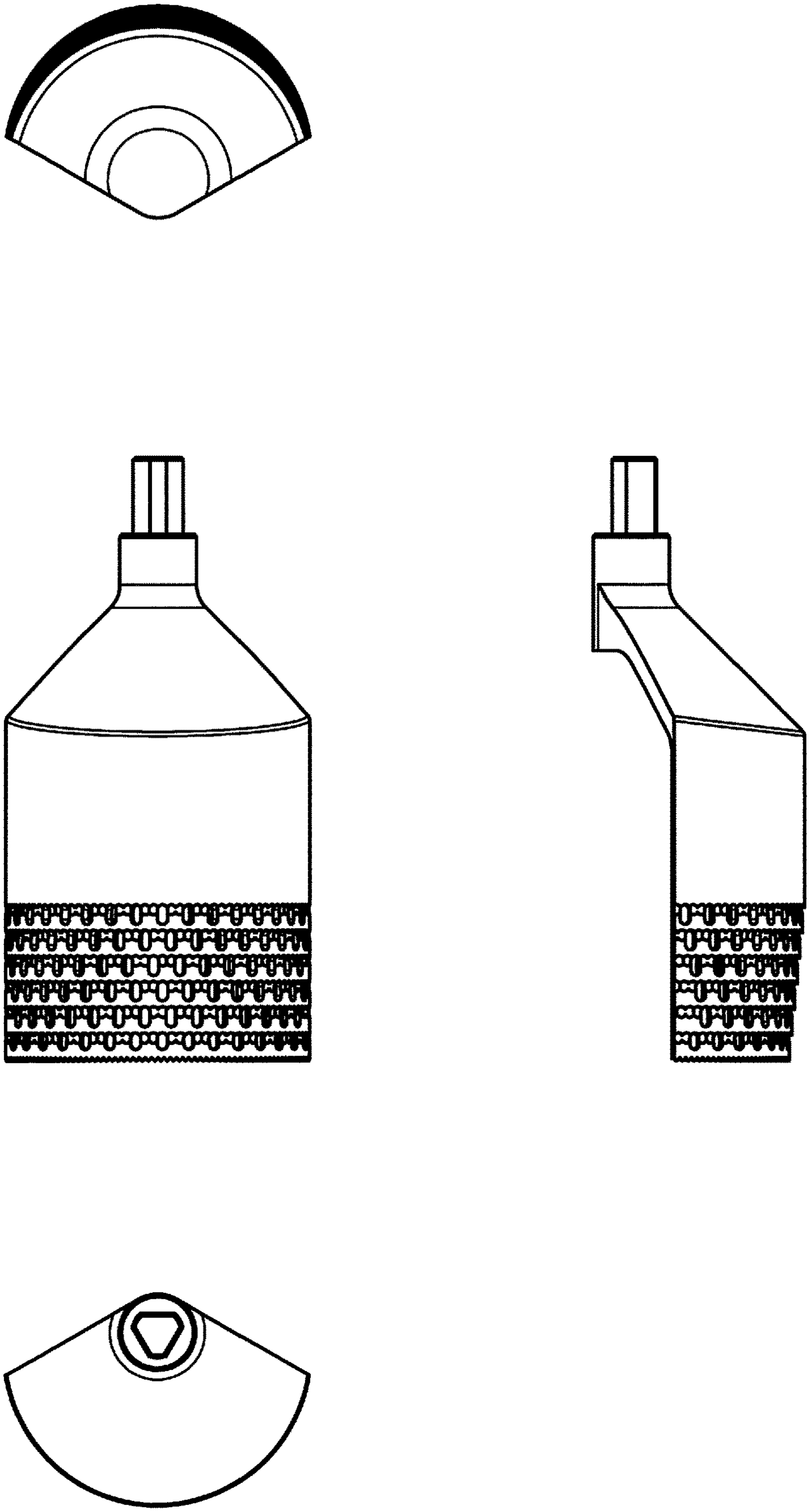
FIG. 2 shows four orthogonal views of the TPLO saw blade.

FIG. 2 shows four orthogonal views of the saw blade according to the present invention.

Figure 3:
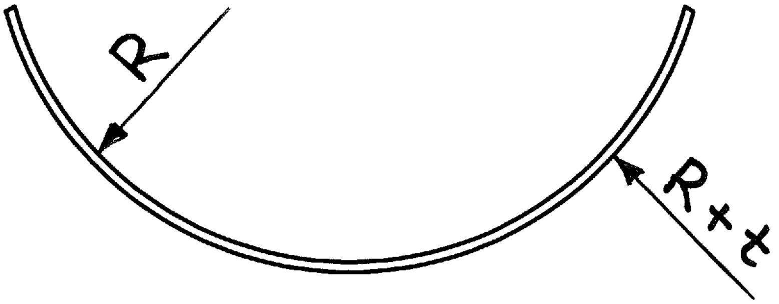
FIG. 3 shows cross-sections of the TPLO saw blade near its leading edge and at the level with the fully developed biradial feature.
Figure 3:
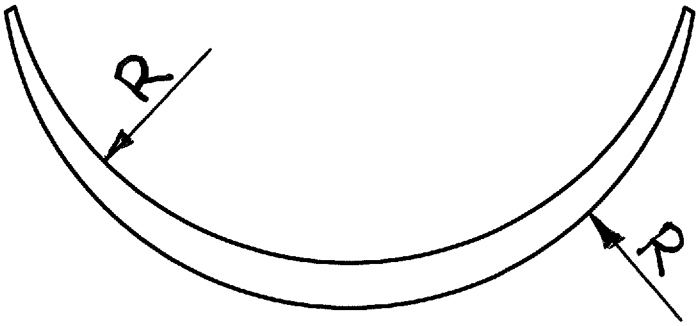

FIG. 3*a* shows the blade shape at the leading edge. The radius R defines the shape of the proximal tibia segment after the osteotomy is performed. The radius on the outside of the saw blade leading edge is (R+t) where t is the thickness of the blade. The lateral side of the TPLO osteotomy of the distal segment will thus have this slightly larger radius and thus will not perfectly match the proximal segment. However, as already mentioned, on the lateral side the cortices will cross at only two points and this mismatch is of minimal consequence.

FIG. 3*b* shows the blade shape at the end of the stepped, cutting part of the saw blade. With careful design, it is possible to make the radius of the convex side be identical to that of the concave side. This is at approximately the level of the medial cortex when the osteotomy is completed. TPLO rotation here results in much longer potential contact and having the radii of the bone segments match provides some advantage to bone healing as advocated by Slocum.

Figure 4:
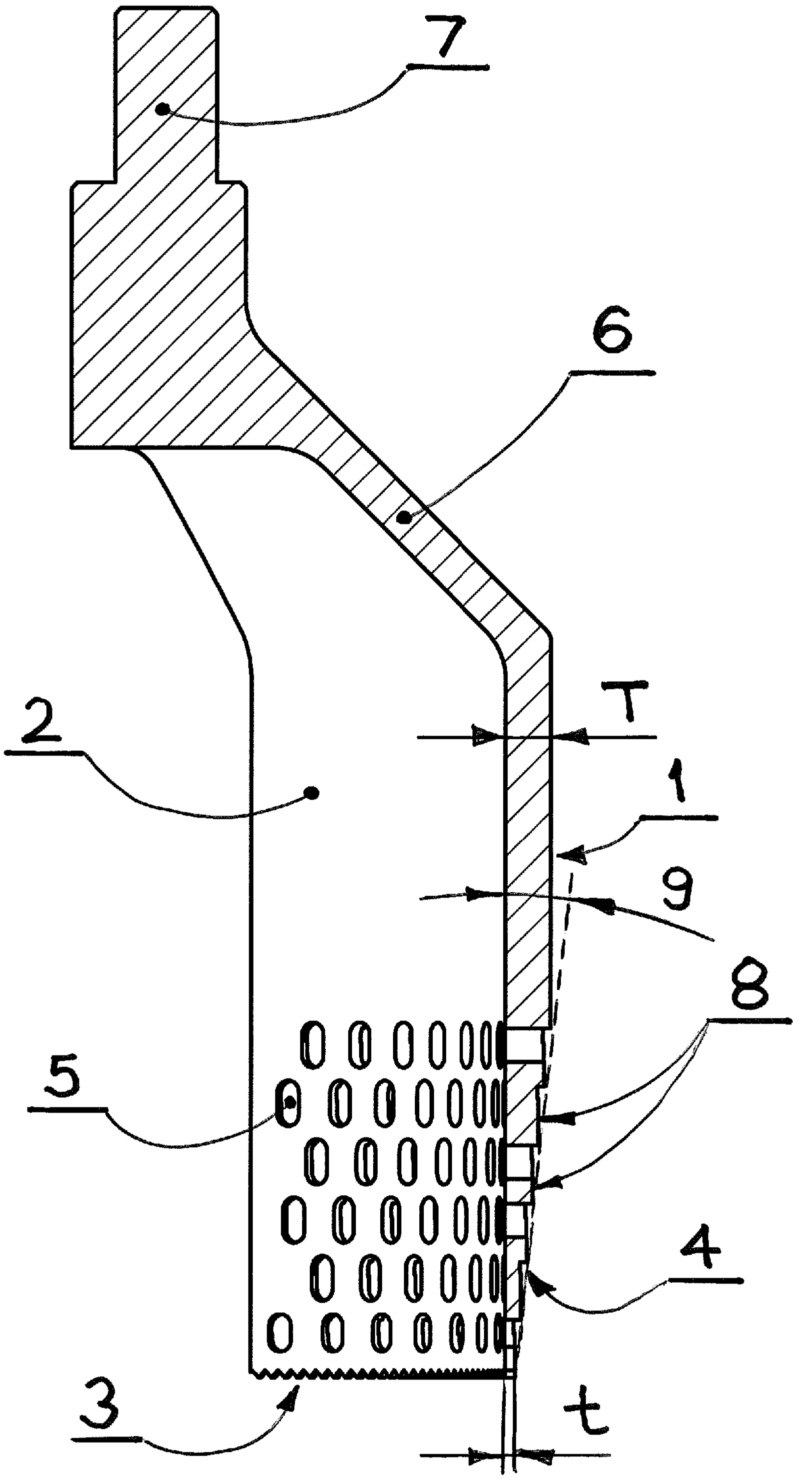
FIG. 4 is a longitudinal cross-section of the TPLO saw blade.

FIG. 4 shows a longitudinal cross-section of the blade. Steps 8 reduce the thickness T of the blade in the mid-plane at the proximal end of the cutting features, to the thickness t at the leading edge. Cutting teeth 4 are formed along the leading edges of steps 8. This results in an approximate wedge-shaped cut of an angle 9. The blades can be produced with angles in increments of 2 to 3 degrees, within the range of 2 to 6 degrees. The saw blade can be manufactured with steps 8 of 0.1 mm to 1.0 mm, depending on the size of the blade, particularly its radius of curvature R, and the desired wedge angle 9. One of the most commonly used TPLO blades has the radius of curvature of 24 mm. For that blade and the wedge angle of 5 degrees, a practical step size is 0.4 mm with the thickness at the leading edge of 0.7 mm.

Figure 5:
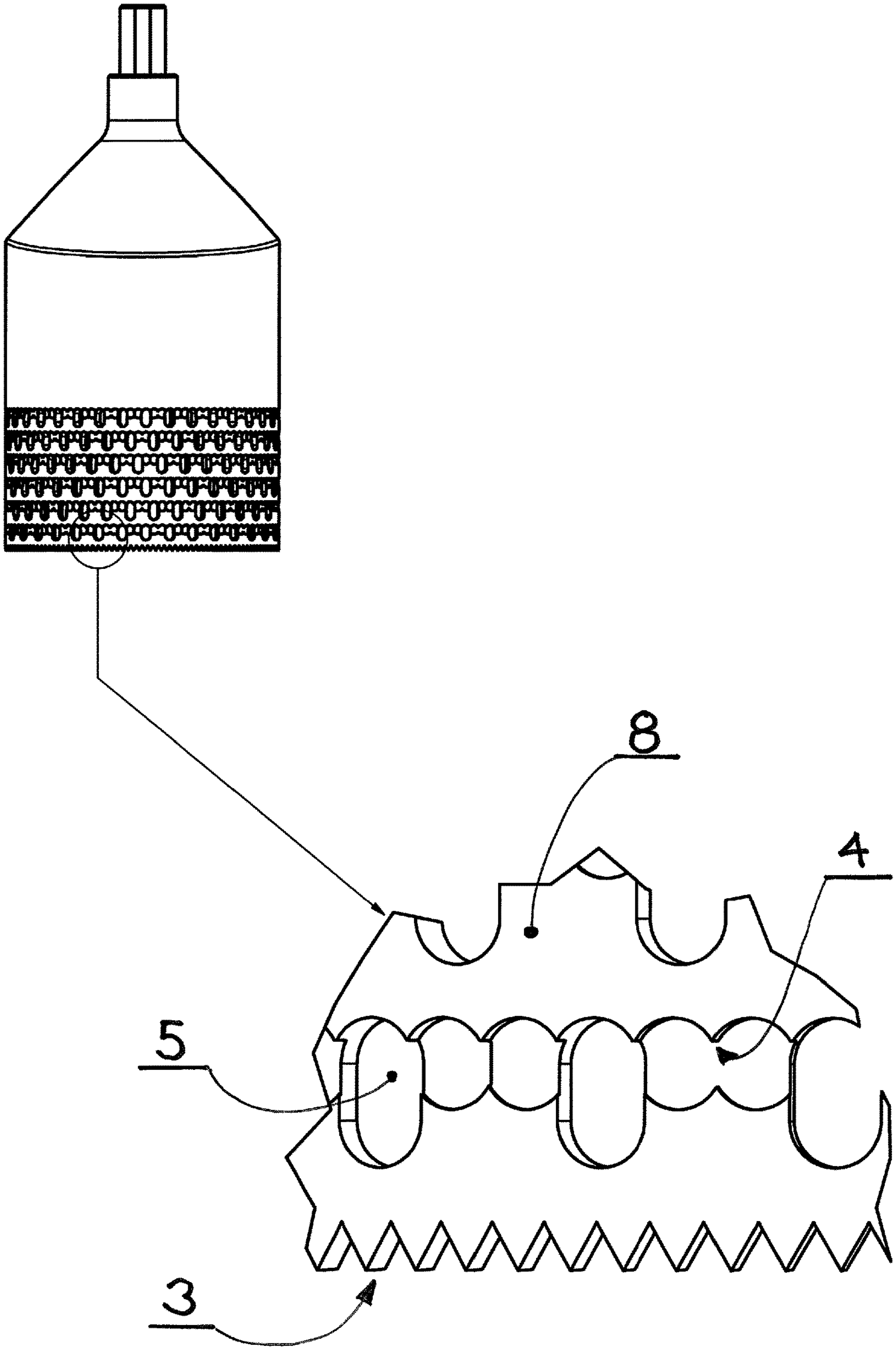
FIG. 5 shows a detail of the TPLO saw blade.

FIG. 5 shows a detail of the saw blade at the leading edge with the teeth 3, the openings 5 and the outside cutting teeth 4 along the leading edges of the steps 8.

Figure 6:
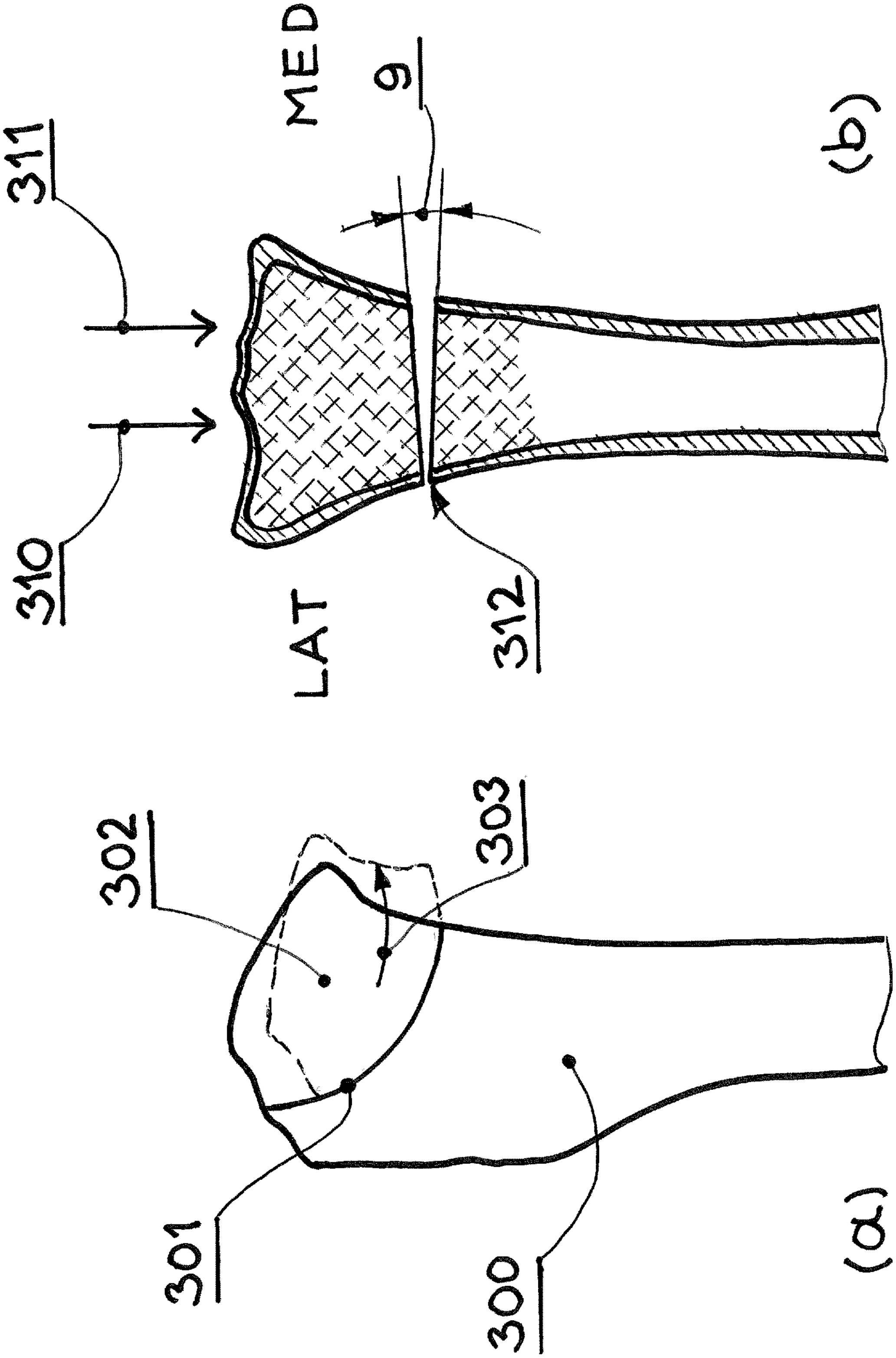
FIG. 6 shows the medio-lateral view of the tibia and its cross-section in the frontal plane with a completed TPLO cut.

FIG. 6*a* shows the medio-lateral view of the proximal tibia 300 with the TPLO osteotomy 301. The proximal segment 302 is rotated by an angle 303 to reduce the instability due to the failure of the cranial cruciate ligament. FIG. 6*b* shows a cross-section of the tibia in the frontal plane after the osteotomy is performed by the blade of the present invention. The resulting wedge 9 of bone removed will be closed by application of the TPLO plate, hence the term closing-wedge osteotomy. The compressive joint reaction 310 will be shifted medially to 311, reducing the loading of the critically weak support 312 on the lateral cortex.

Figure 7:
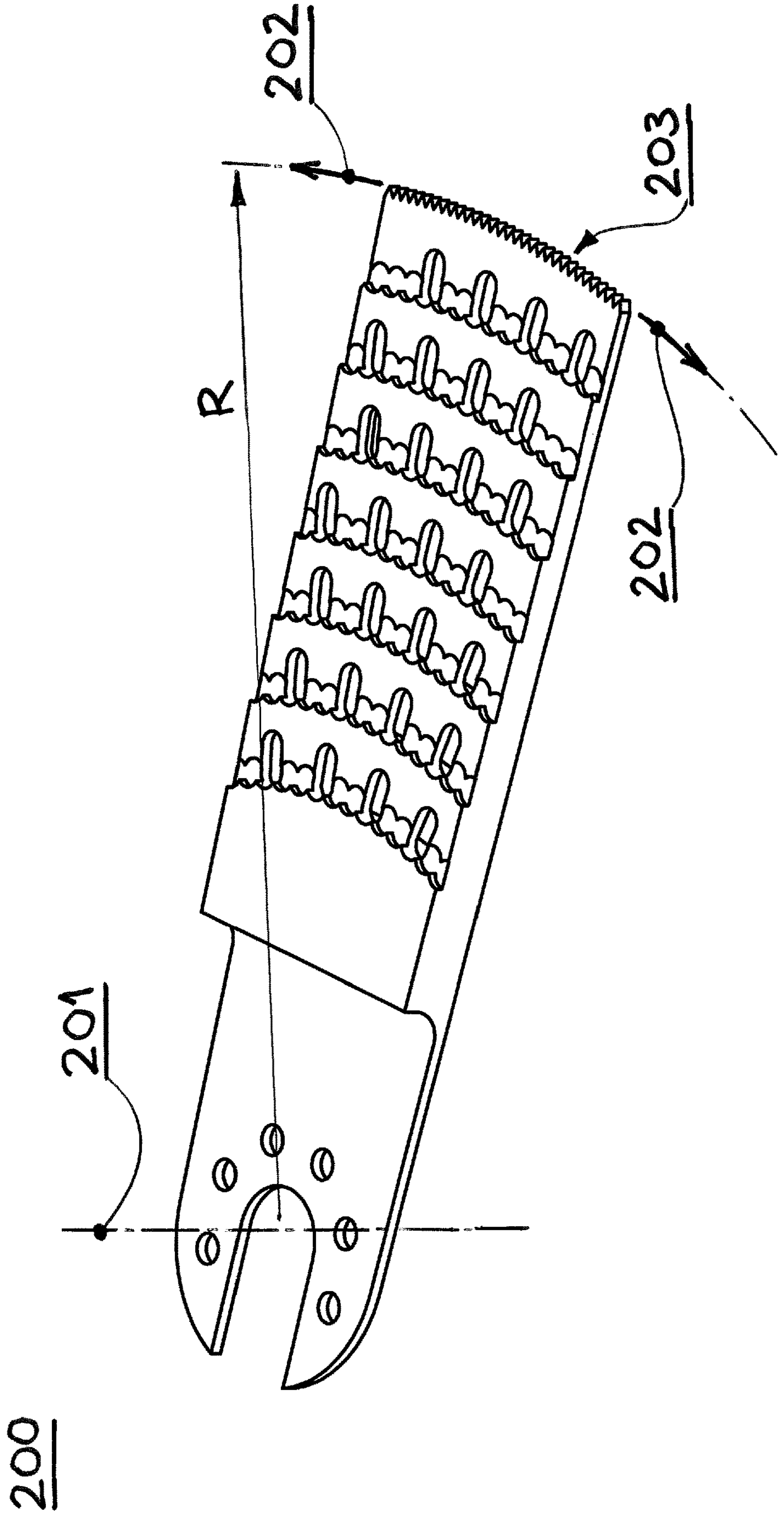
FIG. 7 shows a perspective view of a planar, closing wedge oscillating saw blade.

FIG. 7 is a perspective view of the planar saw blade 200 with the same features of the TPLO saw blade disclosed above. The blade cuts by oscillating movement 202 around the axis 201. The leading edge of radius R is provided by cutting teeth 203.

Figure 8:
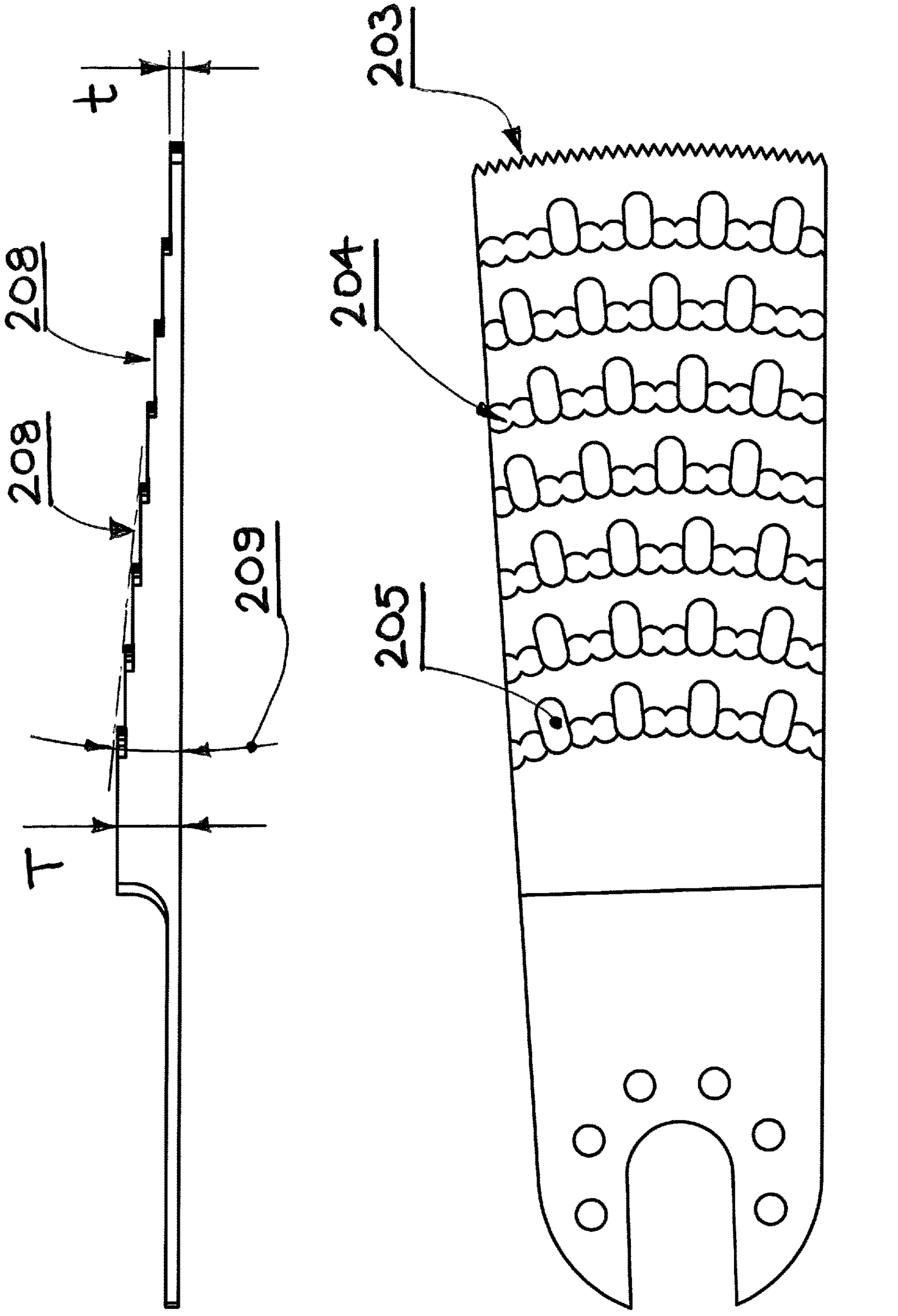
FIG. 8 shows orthogonal views of the planar, closing wedge oscillating saw blade.

FIG. 8 shows orthogonal views of the planar saw blade 200. The blade thickness is increasing by steps 208 from the leading edge thickness t to the end thickness T. This results in an approximate wedge angle 209. For practical applications in bone surgeries, the blades can be manufactured with the wedge angle in 2 to 3-degree increments, with the range covering 2 to 10 degrees. Windows 205 facilitate bone debris removal produced by the leading edge teeth 203 and the trailing, step-to-step, teeth 204.

Having disclosed at least one embodiment of the present invention for a TPLO saw blade and a planar oscillating blade, variations will be understood by one of ordinary skill in the art. Such adaptations, modifications, and improvements are considered part of the invention.

The invention claimed is:

1. An oscillating saw blade adapted for bone surgery, wherein a thickness of the saw blade increases step-wise from a saw blade leading edge at a lower end of the saw blade towards an upper end of the saw blade in a series of steps, wherein the saw blade is of curved shape, the saw blade comprises cutting teeth at the saw blade leading edge and at leading edges of each step; and wherein the saw blade further comprises windows along the leading edge of each step for facilitating bone debris removal;

wherein the windows are at least partially defined by cutting teeth at each step, and a proximal portion of each window is bordered by cutting teeth; and wherein the blade further comprises a concave surface and a convex surface with the radius of curvature of the concave surface equal to the radius of curvature of the convex surface, and the steps and the associated cutting teeth are on the convex surface of the saw blade.

2. The saw blade of claim 1, wherein the curved shape is adapted for use in a Tibial Plateau Leveling Osteotomy TPLO procedure.

3. The saw blade of claim 1, wherein the blade thickness at the saw blade leading edge is uniform while the blade thickness increases in steps away from the leading edge but not along its longitudinal edges.

4. The saw blade of claim 3, where a shape of a cross-section at a trailing end of the blade is of biradial, Slocum type.

5. A planar closing wedge osteotomy procedure, comprising cutting a bone with the saw blade of claim 4.

6. The saw blade of claim 1, wherein the steps are in the range of 0.1 to 1.0 mm.

7. The saw blade according to claim 1, wherein an angle corresponding to the increase in thickness is in the range of 2 to 10 degrees.

8. A Tibial Plateau Leveling Osteotomy (TPLO) procedure, comprising cutting a bone with the saw blade of claim 1.

9. The saw blade of claim 1, wherein the steps are in the range of 0.3 to 0.5 mm.

10. The saw blade of claim 1, wherein the steps are in the range of 0.4 mm.

11. The saw blade according to claim 1, wherein an angle corresponding to the increase in thickness is in the range of 5 degrees.

12. The saw blade according to claim 1, wherein a window at a given step shares a wall extending through a thickness of the saw blade with two consecutive teeth at the given step.

13. The saw blade according to claim 1, wherein the windows are spaced apart by three teeth.

14. The saw blade according to claim 1, wherein the windows are arranged in rows, and the rows of windows are circumferentially offset from each other on the saw blade.

15. The saw blade according to claim 1, wherein, moving in a distal direction, the windows comprise distal end portions that are spaced proximally from the subsequent step.

16. The saw blade according to claim 1, wherein the leading edge comprises a larger number of cutting teeth than the number of cutting teeth at each step.

17. The saw blade according to claim 1, wherein cutting teeth are aligned with outermost side walls of each window.

18. A saw blade adapted for bone surgery, wherein the blade is planar, wherein a thickness of the blade increases from a leading edge at a lower end of the blade towards an upper end of the blade, wherein the leading edge is of a radius around an axis and provided with cutting teeth, and wherein the thickness of the blade increases in a step-wise manner from the leading edge, each step comprising windows for facilitating bone debris removal produced by the leading edge teeth and cutting teeth at leading edges of each step, wherein the windows are at least partially defined by cutting teeth at each step and a proximal portion of each window is bordered by cutting teeth such that cutting teeth are aligned with outermost side walls of each window.

* * * * *